(12) United States Patent
Hakanson et al.

(10) Patent No.: US 6,458,980 B1
(45) Date of Patent: Oct. 1, 2002

(54) CHELATING AGENTS AND THEIR MANGANIC CHELATES

(75) Inventors: Christer L. Hakanson, Helsingborg (SE); Martin Heus, Arnhem (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/462,396

(22) PCT Filed: Jul. 1, 1998

(86) PCT No.: PCT/EP98/04179

§ 371 (c)(1),
(2), (4) Date: Apr. 7, 2000

(87) PCT Pub. No.: WO99/02487

PCT Pub. Date: Jan. 21, 1999

(30) Foreign Application Priority Data

Jul. 9, 1997 (EP) .............................. 97202129

(51) Int. Cl.[7] ...................... C07F 13/00; C07C 251/20; C07C 251/24; C05D 9/02
(52) U.S. Cl. .......................... 556/49; 568/14; 568/707; 562/14; 562/487; 562/488; 556/32; 556/34; 556/45
(58) Field of Search ............................. 556/32, 34, 45, 556/49; 562/488, 489, 14; 568/14, 707

(56) References Cited

U.S. PATENT DOCUMENTS 5,514,823 A * 5/1996 Kordosky et al. ............. 556/32
5,741,920 A * 4/1998 Eckhardt et al. ............. 556/45

OTHER PUBLICATIONS

W. Köhl, "Ueber die β.β' –Diaminoadipinsäure und eine neue Methode zur Darstellung von γ–Aminosäuren", Berichte 36, 172–175 (1903).

(List continued on next page.)

Primary Examiner—Porfirio Nazario-Gonzalez
(74) Attorney, Agent, or Firm—Richard P. Fennelly

(57) ABSTRACT

Chelating agents (chelants) of the general structure:

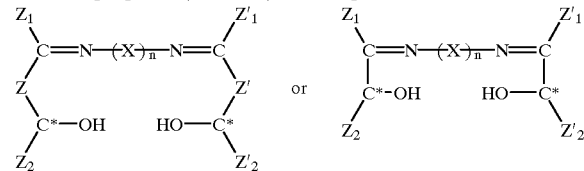

Figure 1:
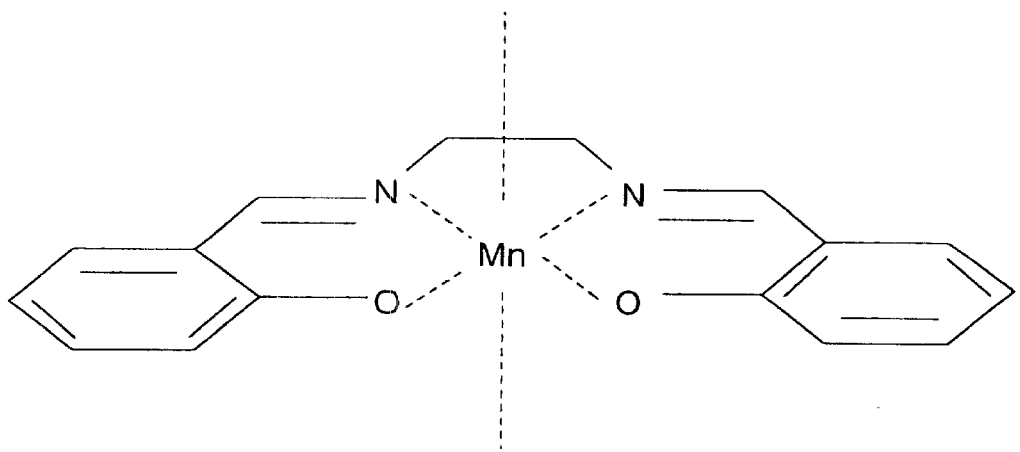

wherein:
n=2–4

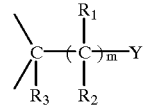

$X = -CR^1R_2-$, or whereby at least two of X are of formula III $Y = COOH$, $-PO_3H_2$ or o-hydroxyphenyl $R_1$, $R_2$ and $R_3$ are independently H or $C_1$–$C_8$ alkyls m=1, 2 or 3 and most preferably m=1

Z and $Z^1$ are unsubstituted or substituted C $C^* = C$ or CH or N $Z_1$, $Z_2$, $Z'_1$, and $Z'_2$ are independently selected from H (or nothing for $Z_2$ and $Z'_2$ if $C^*$ is N) and $C_1$–$C_{10}$ groups that optionally contain one or more N atoms (optionally attached directly to $C^*$), whereby one of the pairs $Z/Z_1$, $Z/Z_2$ and $Z_1/Z_2$ and one of the pairs $Z'/Z'_1$, $Z'_1/Z'_2$ and $Z'/Z'_2$ may be connected to form substituted or unsubstituted (hetero)(poly)cyclic structures of less than 20 atoms.

$C^*$ is either part of an aromatic (hetero)(poly)cyclic structure or linked by a double bond to Z or $Z_2$ and/or Z' or $Z'_2$.

10 Claims, 4 Drawing Sheets

OTHER PUBLICATIONS

J.–H. Liao et al., "Oxidation of Alkenes and Sulfides with Transition Metal Catalysts", Journal of the Chinese Chemical Society, 1995, 42, pp. 847–860.

*International Search Report*, dated Dec. 2, 1998.

* cited by examiner

Soil Test with New Mn Chelate and Other Mn Sources

CHELATING AGENTS AND THEIR MANGANIC CHELATES

The present invention relates to chelating agents, in particular to chelating agents exhibiting selectivity for tri-valent (manganic) manganese ions, to the corresponding manganic chelates, and to their use for the treatment of manganese deficiency in plant cultivation.

Manganese deficiency is a common problem in agriculture, in field crops as well as in fruit orchards, gardening, and other forms of plant cultivation. As a remedy some soils may be treated with manganese salts, usually the sulphate, but the manganese soon forms insoluble oxides which are no longer available to the plants. "Banded" application is therefore recommended, whereas general or broad-cast application is ineffective. In most cases manganese deficiency instead is treated or prevented by foliar application of manganese sulphate.

In the case of other microelements, e.g. iron, deficiencies often are more conveniently treated by general soil application, such as broadcasting or drip irrigation. The metal is kept soluble in the form of a suitable chelate. It has long been desired to find a manganese chelate of such utility. Attempts to use ordinary manganese ($Mn^{2+}$) chelates of known chelating agents like EDTA and DTPA have proved counter-productive, the problem being that the chelating agent is taken over by ferric iron ions from the soil and the manganese set free is soon oxidised to insoluble oxides.

An object of the present invention is to provide a manganic chelate with a high stability with regard to ferric iron ions and other metal ions present in the soil and with regard to decomposition by hydrolysis and, more particularly, to provide a manganic chelate which remains unchanged for an effective period and can therefore be used for the treatment of manganese deficiency by general application to soil and other growing substrates.

The chelating agents (chelants) according to the present invention have the general structure:

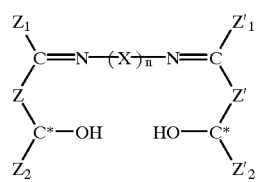

(I)

or

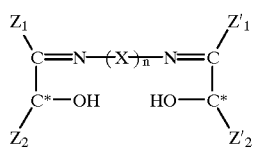

(II)

wherein:
n=2–4

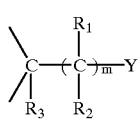

(III)

$X = -CR^1R_2-$, or
whereby
at least two of X are of formula III $Y = COOH$, $-PO_3H_2$ or o-hydroxyphenyl
$R_1$, $R_2$ and $R_3$ are independently H or $C_1$–$C_8$ alkyls
m=0–3, preferably m=1, 2 or 3, and most preferably m=1
Z and Z' are unsubstituted or substituted C
$C^* = C$ or CH or N
$Z_1$, $Z_2$, $Z'_1$ and $Z'_2$ are independently selected from H (or nothing for $Z_2$ and $Z'_2$ if $C^*$ is N) and $C_1$–$C_{10}$ groups that optionally contain one or more N atoms (optionally attached directly to $C^*$), whereby one of the pairs $Z/Z_1$, $Z/Z_2$ and $Z_1/Z_2$ and one of the pairs $Z'/Z'_1$, $Z'/Z'_2$ and $Z'/Z'_2$ may be connected to form substituted or unsubstituted (hetero)(poly)cyclic structures of less than 20 atoms.
$C^*$ is either part of an aromatic (hetero)(poly)cyclic structure or linked by a double bond to Z or $Z_2$ and/or Z' or $Z'_2$.

These aromatic cyclic structures or double bonds are preferably conjugated with the respective $C=N$ bonds to allow each N atom to share the negative charge resulting from dissociation of the OH group.

The inventors have surprisingly found that the hexadentate chelating agents according to the present invention are highly selective chelants for manganic ions in the presence of ferric iron ions and that the manganic chelates also exhibit a remarkable stability with regard to hydrolysis, as well as a good ability to remain soluble in the presence of an iron-containing soil.

More specifically, the manganic chelates according to the present invention have been found to form stable solutions up to a pH of 10.5–11, indicating a pKa for hydrolysis of at least about 11. The ferric chelates of the same chelating agents exhibit stability up to a pH of about 8–9.

Alkaline, neutral or weakly acidic soils are usually more or less aerated. When manganese is applied to such a soil, it will slowly, but inevitably be oxidised to insoluble manganese dioxide. However, if the manganese is very strongly chelated, it can, in principle, be kept soluble and available to the plants for a sufficient time, e.g. weeks or months.

To uphold such strong chelation of manganese ions requires high stability of the chelate with regard to hydrolysis, especially at a high soil pH. At least as important is a high stability with regard to other metal ions that may compete for the chelant and thereby set free manganese ions. This problem is especially critical and well-known with ferric iron ions, which tends to be abundant in soils. Due to its tri-valent positive charge, ferric iron ions is known to form very stable chelates with most chelating agents, e.g. EDTA or DTPA. For manganese, the normal state is the divalent manganese cation, which forms chelates of much lower stability than ferric iron ions. Consequently, it is well-known that manganous chelates when applied to soil are rapidly decomposed, and made useless, by ferric iron ions in the soil.

An interesting option would be to use a chelate of tri-valent (manganic) manganese, which is known to form some chelates of the same order of stability as ferric iron ions. The phenolic chelating agents, e.g. EDDHA (EHPG), long used in the form of their ferric chelates on alkaline soils, would be candidates for forming manganic chelates of fair hydrolytic stability, but the inventors have found that in the presence of an iron-containing soil these manganic chelates will decompose rapidly.

This is in accordance with the findings reported by Ahrland, Dahlgren, and Persson (*Acta Agric. Scand,* 4:101–111, 1990). These authors report that manganic chelates generally are more prone to hydrolysis than ferric chelates. For manganic EDDHA (EHPG) a pKa value of 9.3 is reported for hydrolysis, whereas results according to the present invention indicate a corresponding pKa for the new chelates of at least 11. For ferric iron ions the situation is the reverse. A pKa value for hydrolysis of 12.7 is reported by the same authors, whereas the chelate according to the present invention has a pKa for ferric iron ions of about 9–10.

A manganic chelate with a stability of approximately the same order as that of the ferric chelate will allow a considerable proportion of manganic ions to be set free in the soil. A chelant is sought with a high selectivity for manganic ion over ferric ion. A very high stability of the manganic chelate is important, since the formation of insoluble manganese oxides will be accelerated by a so-called dismutation of two manganic ions to form one manganous ion and one mole of manganese dioxide. Certain soil bacteria also promote the oxidation of soil manganese to the dioxide.

Not wishing to be bound by any theory, the inventors believe the selectivity of the chelating agents according to the present invention to be found in the distorted configuration of the manganic ion in many of its compounds. While the ferric ion always prefers to co-ordinate in a regular octahedral (hexadentate) fashion, the manganic ion is known to display so-called Jahn-Teller distortion. The effect is that two opposite ("axial") bonds tend to be elongated in comparison with the remaining four ("equatorial") bonds. It is thought, in order to explain the selectivity of the chelating agents according to the present invention, that the two positions where the axial coordinating groups branch out are more or less locked by a rigid structure including the four equatorial bonds. With such restrictions on the two axial coordinating groups, the importance of the elongated manganic valences is understandable.

In one of the preferred manganic chelates of the invention the rigid, equatorial structure is thought to be formed by the phenolic and iminic groups in the well-known salen structure (short for salicylaldehyde-ethylenediamine adduct), which is known to prefer a stable, planar structure in its metal chelates, as shown in FIG. 1.

The negative charges are partly delocalised from the phenolic oxygen to the imine nitrogen. This resonance serves to favour the rigid, planar structure. The complete chelate has two carboxymethyl groups on the N-N bridge (FIG. 2).

Said N-N bridge may be formed by the condensation of one molecule of 3,4-diamino-1,6-hexanedioic acid with two molecules of salicylaldehyde. Due to the rigid salen structure the two carboxymethyl groups are restricted in the ways in which they can occupy the two axial valences of the metal ion. This is most probably the feature that favours the elongated axial valences of the manganic ion over those of the ferric ion.

Figure 2:
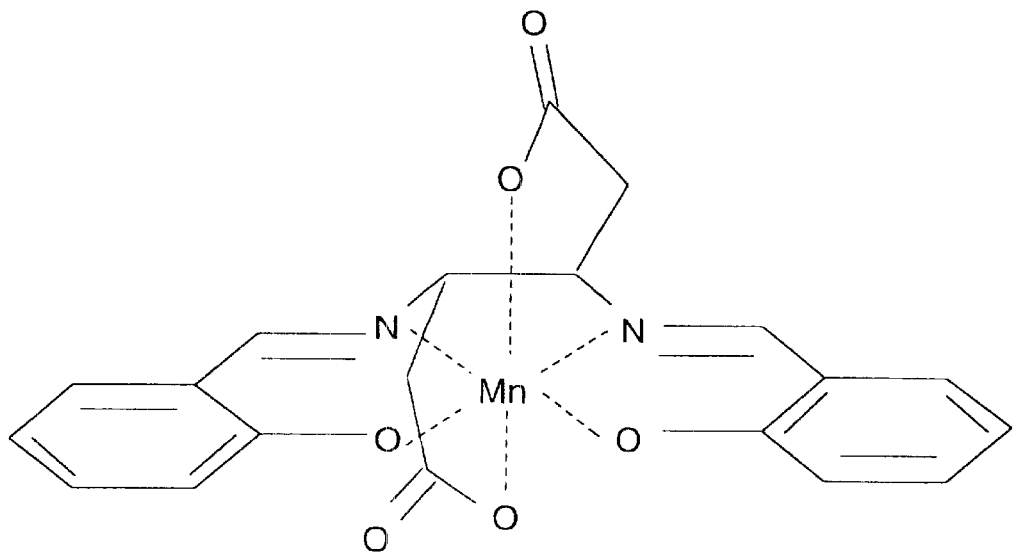
Figure 3:
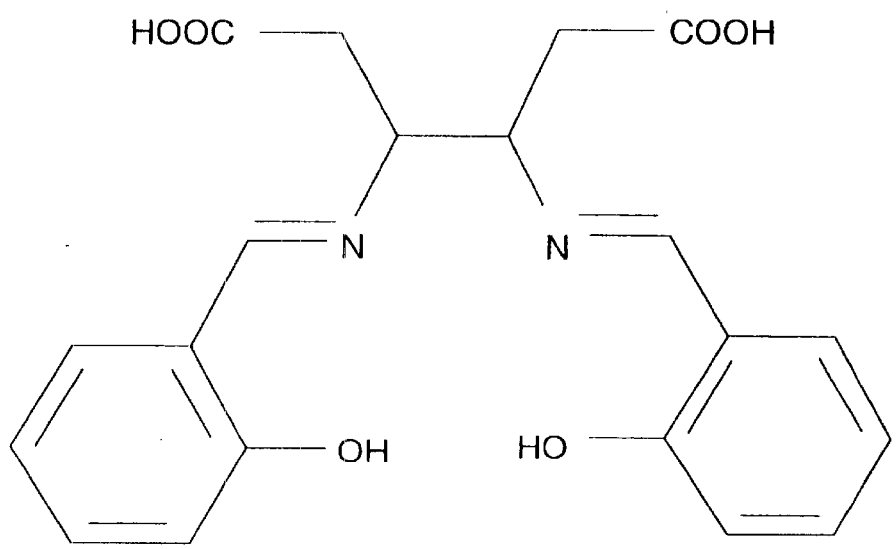

The chelating agent of FIG. 2 is depicted in a 2-dimensional way in FIG. 3.

The two carbon atoms joining the nitrogen atoms are both asymmetrical, and the molecule can therefore occur in two diastereo-isomers. The one depicted in FIG. 3 is the racemic isomer, which is believed to be produced as described in Example 1 (see below). The meso-isomer will give rise to a different geometry, but may also be of value.

For comparison, the corresponding chelating agent with secondary amino functions instead of the imine groups was prepared by reduction with sodium borohydride (see below). The manganic chelate of the reduced product proved to be very unstable to hydrolysis. Manganese dioxide started to precipitate immediately at neutral pH.

Figure 4:
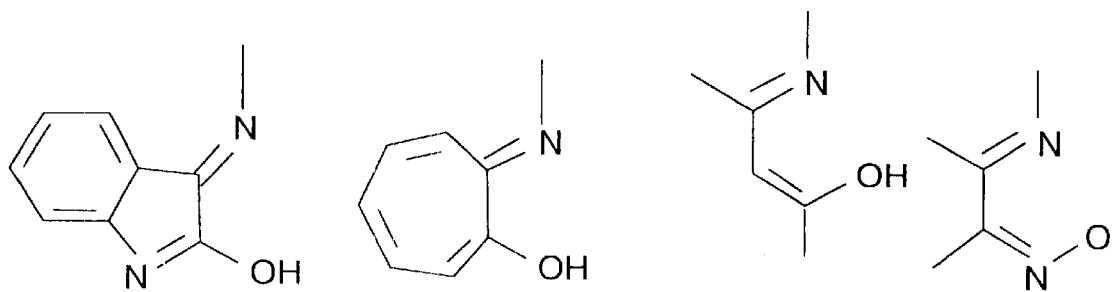

In addition to the salen structure, other four-dentate chelating units containing two imine nitrogens and two hydroxylic anions can enclose the manganic ion in a similar way and form the basis of chelating agents with a corresponding selectivity to manganic ion. Some of the most elementary examples are those with various substituents in the two benzene rings, but more essential variations in the structure will also produce a similar effect. A moderate variation is the use of pyridoxal (2-methyl-3-hydroxy-5-hydroxymethyl-4-pyridinaldehyde) instead of salicylaldehyde. More substantial variations include the hydroxyimines formed by such hydroxy-oxo compounds as shown in FIG. 4.

With isatin (FIG. 4a) and tropolone (FIG. 4b) the 6-membered chelate rings of the salen structure will be replaced by likewise resonance-stabilised 5-membered chelate rings. The chelates will comply with the general structure II shown earlier.

Another variation is to use a different diamino diacid as the central building block in the di-imine structure. While 3,4-diamino-1,6-hexanedioic acid has a two-carbon chain joining the two nitrogens, it is possible within the scope of the invention to increase this chain length to 3 or even 4 while still retaining an adequate stability and rigidity of the structure (n=2–4 in the general structure defined).

It is also possible to modify the positioning of the two carboxyl groups that will form the two axial bonds. This can be done by varying the length of the chains that connect the two carboxyl groups to the carbons linking the two nitrogen atoms. This chain length, with m=1 in the chelant made from 3,4-diamino-1,6-hexanedioic acid, can be varied from 0 to 3 while still retaining the interaction with the elongated axial valences of the manganic ion. Preferably m=1, 2, or 3. Most preferably m=1.

A final type of variation in the chelating agent of the invention is replacing the carboxyl groups with other acidic coordinating groups such as phosphonyl ($-PO_3H_2$) or 2-hydroxy-phenyl.

Figure 6:
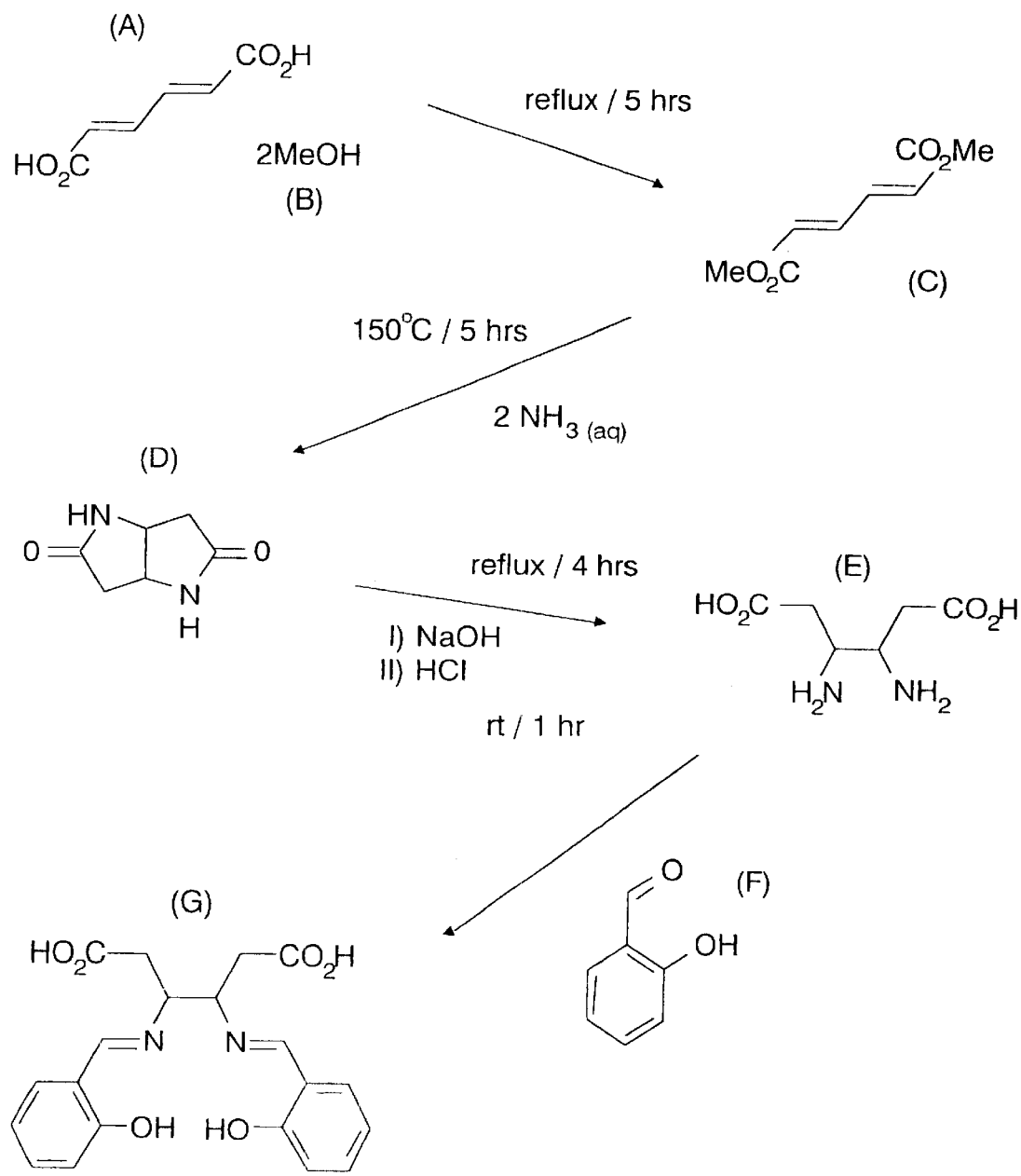

A synthesis route for a further manganese selective chelate according to the present invention is shown in FIG. 6.

Experimental

The experimental hydrolytic stability of the new manganic chelates was demonstrated in a shaking test with calcium carbonate in which the new manganic chelate stayed completely soluble for at least several weeks.

The inventors demonstrated the selectivity of the new chelating agents by means of comparative experiments with ferric and manganic ions at near neutral pH. The new chelant showed a remarkable preference for manganic ion, as shown by the yellow colour remaining stable for at least several weeks.

Consequently, the new manganic chelate has the qualities required for soil application. This has been demonstrated in comparative tests with other manganese chelates using an actual iron-containing soil. Dilute solutions of the new manganic chelate and of the other manganese sources were treated with a typical soil having a low manganese content but a high iron content. With the new manganic chelate the soluble manganese decreased very slowly and retained about 50% of its original content after 19 days, whereas all the other Mn chelates tested were largely insolubilised after 1–2 days.

The soil tests demonstrate that the new manganic chelates will remain dissolved in the water phase of the soil. They will therefore be mobile and will be able to migrate and reach the roots of plants. The roots will most certainly be able to absorb the manganese in the divalent (manganous) form after creating a local reducing environment and lowered pH. This is the strategy plants are known to use to destabilise chelates of ferric iron ions and absorb the iron.

The products of the invention and the results obtained are further detailed in Examples 1–8.

Synthesis of the Novel Chelates

The di-imine chelating agents of the invention were prepared by the condensation of one molecule of an appropriate diamino compound, having two acidic groups attached as defined above, with two molecules of a suitable hydroxy-oxo compound as defined above, or a suitable derivative thereof.

The manganic chelates can be produced using an already tri-valent manganese salt such as the acetate, $Mn(OAc)_3$. An alternative method is to first prepare a manganous chelate by the use of, e.g., manganous sulphate and then to oxidise to the manganic state with air or by adding an oxidant such as potassium permanganate or manganese dioxide.

EXAMPLE 1

Synthesis of New Chelant from Salicylaldehyde and 3,4-diaminohexanedioic acid

The bicyclic dilactam of 3,4-diamino-1,6-hexanedioic acid was synthesised via the diamide of muconic acid (2,4-hexadiene-1,6-dioic acid) essentially as outlined by Köhl in *Berichte* 35, 173 (1903). In a modification of Köhl's procedure, the dimethylester of trans, trans-muconic acid (13.6 g=0.080 mole) was autoclaved for 5 hours at 150° C. with 60 ml 32% aqueous ammonia. The resulting solution on evaporation and cooling yielded 1.40 g of crystalline dilactam.

The product was analysed by $H^1NMR$ and the spectrum was in agreement with the dilactam structure. Due to the rigid bicyclic structure it was possible to correlate the NMR spectrum with the diastereomeric structure of the dilactam. The racemic form was found to correlate better with the lactic structure than with the meso form.

0.432 of the dilactam (4 mmoles) was hydrolysed by refluxing for 5 hours with 10 ml 1-N sodium hydroxide. After cooling to room temperature, the solution was acidified with hydrochloric acid to pH 6. The yield of crystalline 3,4-diamino-1,6-hexanedioic acid dihydrate was 0.535 g. It was assumed to retain the racemic structure of the dilactam.

0.180 g of the 3,4-diamino-1,6-hexanedioic acid dihydrate (0.85 mmole) was dissolved in 15 ml water with the aid of 2 ml 1-N sodium hydroxide to a pH of 10. Next 0.244 g salicylaldehyde (2.0 mmoles) was added, and the mixture was stirred at 30° for 30 minutes. The progress of the condensation reaction was shown by a drop in pH and by the development of a yellow colour. Some extra sodium hydroxide was added to keep the pH over 8. The final pH was 8.6. The yellow solution was diluted to 25 ml to obtain a concentration of 0.04 mmole chelant per ml.

EXAMPLE 2

Manganic Chelate of the Chelant 2 ml of the chelant solution from Example 1 (max. 0.08 mole) was diluted with 30 ml water to give a pH of 8.5. 2 ml of a 0.02 molar solution of manganous sulphate (0.04 mmole) was added to give a pH of 7.9. Finally, 2 ml of 0.0005 molar potassium permanganate (0.01 mmole) was added dropwise in order to transform all manganese to the tri-valent stage (eventually 0.05 mmole Mn). A brown colour developed, which changed to a stable yellow ochre in the course of 15 minutes. The final pH was 8.0.

EXAMPLE 3

Hydrolytic Stability of the New Manganic Chelate

The manganic chelate solution from Example 2 was alkalised step-wise with dilute sodium hydroxide. Samples were taken at various pH and set aside for later inspection. The results can be seen in the following table:

| pH | immediately | after 1 h | after 24 hours | after 6 days |
|---|---|---|---|---|
| 8 | clear ochre yellow | clear, same colour | clear, same colour | clear, same colour |
| 9 | clear, same colour | clear, same colour | clear, same colour | clear, same colour |
| 10.5 | clear, same colour | clear, same colour | clear, same colour | clear, same colour |
| 11 | clear, same colour | clear, same colour | slight precipitate | slight precipitate |
| 11.3 | clear, same colour | precipitation starting | considerable dark precipitate, light yellow solution | as before |

This example demonstrates that the new manganic chelate is stable to hydrolysis up to a pH of at least 10.5.

EXAMPLE 4

Comparative Test with a Reduced Chelant

A solution of the chelant according to Example 1 was adjusted to a concentration of 10 mmoles/L and a ph of 5. Sodium borohydride was added at 5 minute intervals until the yellow salicylimine colour disappeared. The pH was then adjusted to 8, and the manganic chelate was generated as described in Example 2 for a final pH of 8. The result was an immediate dark precipitate, presumably manganese dioxide.

EXAMPLE 5

Formation and Hydrolytic Stability of a Ferric Chelate 2 ml chelate solution from Example 1 (0.08 mmole) was diluted with 15 ml water and 1 ml of 0.05 molar ferric chloride solution was added dropwise. The pH was brought to 7 with dilute sodium hydroxide, giving a dark wine red solution. The solution was then gradually alkalised by the addition of dilute sodium hydroxide, and the colour was observed during the next 1–2 hours. The results are shown in Table 1 below:

| pH | Appearance |
|---|---|
| 7 | Wine red |
| 8 | Wine red |
| 9 | Slightly lighter wine red |
| 10 | Lighter wine red |
| 11 | Much lighter wine red |

This example indicates that the ferric chelate of the new chelant has a lower hydrolytic stability than the manganic chelate, since it starts to hydrolyse already at pH 9.

EXAMPLE 6

Stability of the New Manganic Chelate as Compared with Ferric Iron Ions

In order to show the preference of the new chelants for manganic ions over ferric ions, stable, slightly alkaline solutions of these ions were by chelation with two moies of citric acid. Both solutions were adjusted with sodium hydroxide to a pH of 7.8 at a concentration of 0.001 mmole/ml of manganese and iron, respectively. Three experiments were made for comparison:

a) of each solution 10 ml (0.01 mmole) was mixed, and 0.25 g of the 0.04 molar chelate (or ligand) solution from Example 1 (0.01 mol) was added.

b) 10 ml of manganic citrate solution was mixed with 0.25 g of the chelate solution.

c) 10 ml of the ferric citrate solution was mixed with 0.25 g of the chelate solution.

Both a) and b) developed a yellow ochre colour typical of the manganic chelate as reported in Example 2, whereas c) developed a red colour. The yellow colour of a) and b) was stable for weeks, apparently indefinitely so. For c) the solution turned completely red in about one hour.

EXAMPLE 7
Soil Tests with the New Manganic Chelate and Other Manganese Sources A soil sample was taken from a sugar-beet field in Helsingborg, Sweden. It was sifted and homogenised and analysed by a certified agricultural laboratory by so-called ICP after extraction with dilute acetic of EDTA. It was found to contain 1.6 mg manganese, 379 mg iron, and 970 mg calcium per litre of soil and had a pH of 7.1.

35 g portions of the slightly moist soil were transferred to 250 ml glass bottles together with 120 ml of dilute solutions containing about 30 ppm manganese. The solutions to be tested were made from:

the new manganic chelate solution of Example 2;

a manganic chelate of EDDHA (ethylenediamine-di-2-hydroxyphenylacetic acid)

a manganic chelate of DTPA (diethylenetriaminepentaacetic acid)

a manganous chelate of EDTA (ethylenediaminetetraacetic acid)

manganous sulphate ($MnSO_4$)

Figure 5:
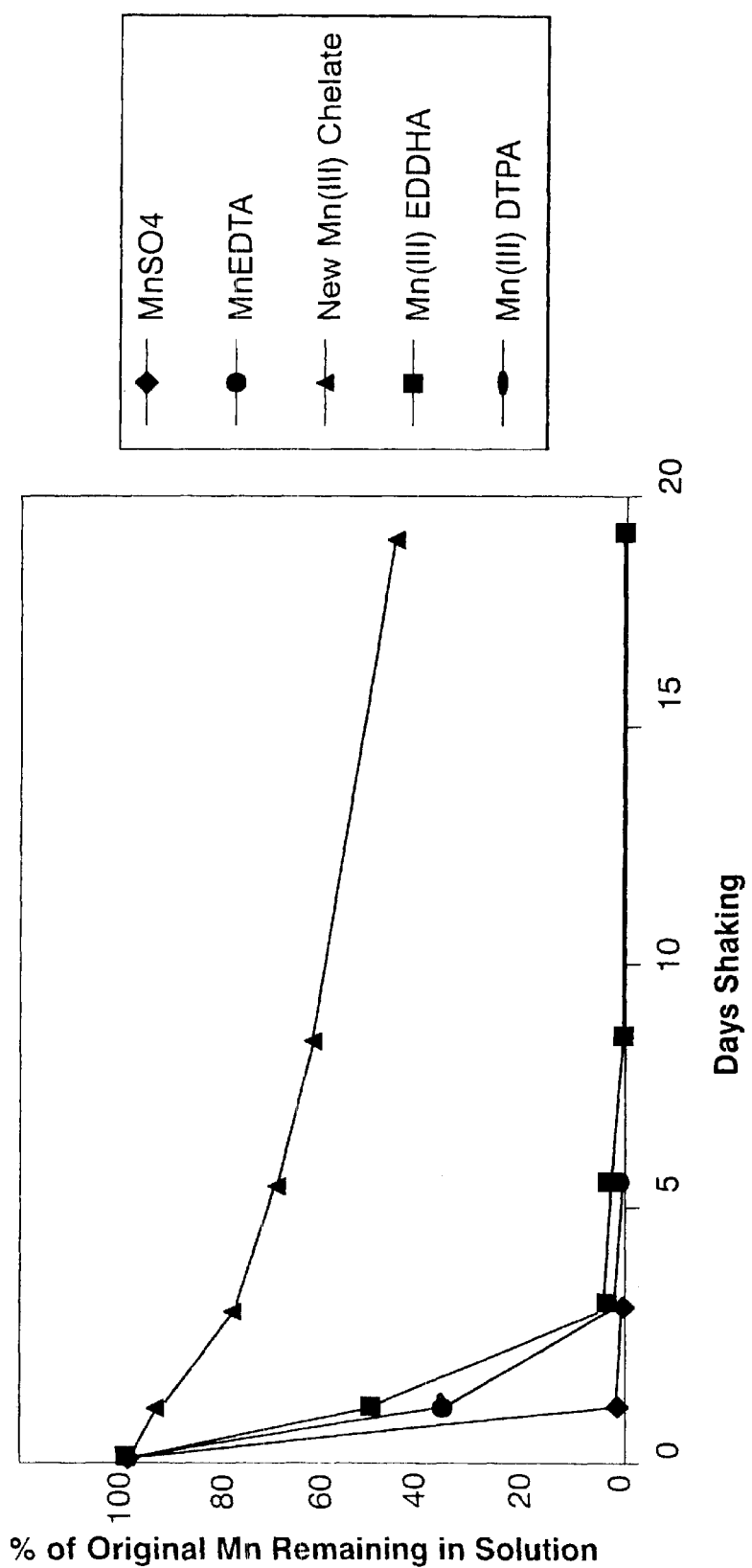

The bottles were rotated in a tumbling device at about 1 revolution per second for a period of 19 days. Samples were taken at intervals and clarified by centrifuging for about one hour in a test-tube centrifuge. The clear liquid samples were analysed by ICP. The results are shown in FIG. 5.

The colours of the centrifuged samples indicated that the lost manganese had been replaced by ferric iron ions. This was especially visible for the manganic chelates of the new chelate and of EDDHA, which both form a red colour with ferric iron ions. In the soil test with manganic EDDHA the brownish colour had changed to red already after 1 day, whereas the new manganic chelate only displayed a visible change to orange yellow after a week.

EXAMPLE 8
Shaking Test with Calcium Carbonate

The test in Example 6 was repeated with the new manganic chelate but with analytical grade calcium carbonate instead of soil. The pH of the suspension was 8.5. The manganese content in the liquid phase remained constant at the 30 ppm level for several weeks and the colour remained the same yellow ochre. This shows that the new manganic chelate has an excellent hydrolytic stability at pH 8.5 in the presence of calcium.

EXAMPLE 9
New Chelant Using Tropolone Instead of Salicylaldehyde

Tropolone methyl ether has a reactivity corresponding to that of a carboxylic ester.

0.408 g of the methyl ether (3.0 mmoles) was added to a solution of 0.264 g 3,4-diaminohexanedioic acid (1.5 mmoles), and 0.020 g sodium hydroxide (5.0 mmoles) in 10 ml of methanol. After stirring for 10 minutes at room temperature, 2.5 ml water was added to dissolve all solids. After stirring for another 2 hours the solution was evaporated to dryness (40°, 20 mbar). The resulting yellow solid chelant weighed 0.50 g after washing with ethyl acetate and drying. The NMR was in agreement with the expected bis-imine from tropolone and 3,4-diaminohexanedioic acid.

The manganic chelate of the new chelant was prepared in analogy with Example 2 and formed a brown solution stable at pH 10.

With ferric iron ions the chelant formed a red solution at pH 5. On raising the pH the red colour started to fade at pH 7–8. At pH 10 it turned yellow, with precipitation of the ferric hydroxide.

With molar equivalents of both manganic and ferric ions at pH 9, the chelant displayed a stable brown colour, indicating a preference for manganic ions.

EXAMPLE 10
Synthesis of a Further Manganese Selective Chelate

A compound was synthesised from muconic acid, ammonia, and salicylaldehyde, see FIG. 6. The performance of the product was tested for manganese selectivity over iron.

Muconic Acid (A) was Esterified (Step 1)
Raw Materials

| | |
|---|---|
| muconic acid | 19.9 g (0.14 moles) |
| 2,2-dimethoxypropane | 29 g |
| methanol | 100 ml |
| hydrochloric acid 36% | 3 ml |

Recipe

A one-necked 250 ml roundbottom flask was charged with muconic acid (A) and methanol (B). To the stirred slurry dimethoxypropane and hydrochloric acid was added. The mixture was refluxed for 5 hours. The solvent became light yellow. After cooling to 5° C. the white solid was filtered off and washed with cold methanol. The solid was dried in a vacuum oven at 50° C.

Result: 11.2 g (0.066 moles, 95%) of white powdered muconic acid dimethylester (C), m.p. 155–157° C., purity >98% (NMR)

Synthesis of Dilactam (Step 2)
Raw Materials

| | |
|---|---|
| muconic acid dimethylester (C) | 8.3 g (0.049 moles) |
| ammonia 25% | 100 ml |

A 150 ml autoclave was charged with ammonia and muconic acid dimethylester (C). The autoclave was closed and heated to 150° C. (p=18 bar). The mixture was stirred for 4 hours and cooled to room temperature. The solution was light brown and clear.

After concentration of the solution to ±10 ml on the rotavap, it was stored at 5° C. for 18 hours. The needle-like crystals were filtered off and washed with cold methanol.

Result: 1.6 g (0.011 moles, 23%) of off-white powdered dilactam (D), purity >90% (NMR).

Ring Opening of Dilactam (D) (Step 3)
Raw Materials

| | |
|---|---|
| dilactam (D) | 1.6 g (0.011 moles) |
| sodium hydroxyde | 1.7 g (0.043 moles) |
| water | 30 ml |
| hydrochloric acid 36% | |

Recipe 1.7 g of sodium hydroxide was dissolved in 30 ml water and stirred in a 50 ml one-necked flask.

Dilactam (D) was added to the caustic solution, after which the temperature was raised and the solution refluxed for 7 hours.

After cooling to room temperature, the solution was slowly acidified to pH=6.0. A white precipitate of diaminohexanedioic acid (E) was formed, and the mixture was cooled in an ice bath to 3° C. The white solid was filtered off and dried in a vacuum oven at 50° C.

Result: 1.5 g (0.0085 mole, 77%) of white solid, purity>97% (NMR).

Preparation of a Manganese Chelate Solution (Step 4)

0176 g (1 mmole) of diaminohexanedioic acid (E) was dissolved in 20 ml of water. The pH was adjusted to 10.5 using 4 M NaOH (F).

0.320 g salicylaldehyde was added. The pH was kept at 8.6 by the addition of 4M NaOH. The solution was stirred for 1 hour and made up to 100 ml in a volumetric flask.

In a 100 ml volumetric flask were mixed:

| | |
|---|---|
| 10 ml chelate solution | 10 mM |
| 10 m Mn (II) solution | 10 mM |
| 10 ml permanganate solution | 2.5 mM |

Made up to 100 ml this yielded a 1 mM Mn(III)chelate solution (G) (pH±8). This product (G) was capable of forming a complex with manganese.

The invention is not limited to the above description, the requested rights being defined by the following claims.

What is claimed is:

1. Chelating agents (chelants) of the general structure:

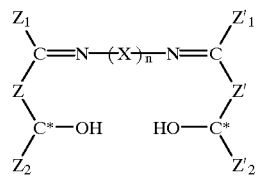

(I)

or

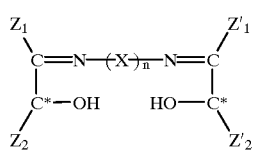

(II)

wherein:

n=2–4

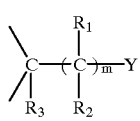

(III)

$X = -CR^1R_2-$, or whereby at least two of X are of formula III $Y = COOH$, $-PO_3H_2$ or o-hydroxyphenyl $R_1$, $R_2$ and $R_3$ are independently H or $C_1-C_8$ alkyls m=1, 2 or 3 and most preferably m=1

Z and Z' are unsubstituted or substituted C $C^* = C$ or CH or N $Z_1$, $Z_2$, $Z'_1$ and $Z'_2$ are independently selected from H (or nothing for $Z_2$ and $Z'_2$ if $C^*$ is N) and $C_1-C_{10}$ groups that optionally contain one or more N atoms (optionally attached directly to $C^*$), whereby one of the pairs $Z/Z_1$, $Z/Z_2$ and $Z_1/Z_2$ and one of the pairs $Z'/Z'_1$, $Z'/Z'_2$ and $Z'_1/Z'_2$ may be connected to form substituted or unsubstituted (hetero)(poly)cyclic structures of less than 20 atoms $C^*$ is either part of an aromatic (hetero)(poly)cyclic structure or linked by a double bond to Z or $Z_2$ and/or Z' or $Z'_2$.

2. The products according to claim 1 wherein the aromatic cyclic structures and/or double bonds are conjugated with the respective C=N bonds, to allow each N atom to share the negative charge resulting from dissociation of the OH group.

3. The products according to claim 1 wherein the desired conjugated imine structure is derived from substituted or unsubstituted salicylaldehyde or from pyridoxal, tropolone, isatin, a beta-diketone or a 2-oximinoketone.

4. The products according to any one of claims 1, 2 or 3 wherein the chelating agent has the specific structure

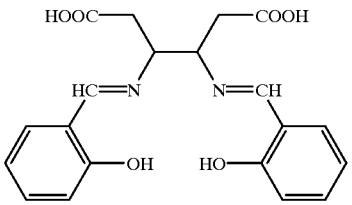

5. The manganic chelates of the chelating agents according to any one of claims 1–3.

6. The use of the manganese chelates according to claim 5 against manganese deficiency in plant cultivation.

7. The production of any of the chelating agents of claim 1 by reacting approximately two molar equivalents of a relevant keto compound with one molar equivalent of an appropriate diamino compound.

8. The production of the chelating agent of claim 4 by reacting approximately two molar equivalents of salicylaldehyde with one molar equivalent of 3,4-diaminohexanedioic acid.

9. The production of the manganic chelates of the invention by reacting the chelating agent with a salt of divalent manganese and oxidising to the trivalent state with air or other oxidants such as permanganate or manganese dioxide.

10. A chelating agent according to claim 1 wherein X is of formula III and Y is COOH.

* * * * *